United States Patent [19]
Breskin et al.

[11] Patent Number: 5,194,738
[45] Date of Patent: Mar. 16, 1993

[54] APPARATUS FOR DIGITAL IMAGING

[75] Inventors: Amos Breskin, Rehovot; Rachel Chechik, Moshav Bet Hanan; Ehud Dafni, Rehovot, all of Israel

[73] Assignee: Yeda Research & Development Co. Ltd., Rehovot, Israel

[21] Appl. No.: 725,618

[22] Filed: Jul. 3, 1991

[30] Foreign Application Priority Data

Jul. 10, 1990 [IL] Israel ......................................... 95033

[51] Int. Cl.$^5$ .............................................. G01T 1/185
[52] U.S. Cl. .................................. 250/385.1; 250/374
[58] Field of Search ............................. 250/385.1, 374

[56] References Cited

U.S. PATENT DOCUMENTS

| | | | |
|---|---|---|---|
| 4,639,601 | 1/1987 | Pullan | 250/385.1 |
| 4,670,656 | 6/1987 | Bolon | 250/385.1 |
| 4,999,500 | 3/1991 | Breskin et al. | 250/385.1 |
| 5,032,729 | 7/1991 | Charpak | 250/385.1 |
| 5,059,802 | 10/1991 | Filthuth | 250/374 |

OTHER PUBLICATIONS

Cattai, A., The Multistep Avalanche Chamber for Beta Radiochromatography Nuclear Instruments and Methods in Physics Research, 215 (1983), pp. 489-492.
Petersen, G. et al., The Multistep Avalanche Chamber as a Detector in Radiochromatography Imaging, Nuclear Instruments and Methods 176 (1980) pp. 489-492.
Bateman et al., An Improved multistep Avalanche Detector System for Digital Audioradiography, Nuclear Instruments and Methods in Physics Research A 264 (1988) pp. 430-435.
Breskin, A. et al., The Multistep Avalanche Chamber: A new Family of Fast High Rate Particle Detectors, Nuclear Instruments and Methods 161 (1982) pp. 19-34.
Breskin, A. et al., A multistep Parallax-free X-Ray Imaging Counter, Nuclear Instruments and Methods 195 (1982) pp. 469-473.
Sauvage, D. et al., A systematic Study of the Emission of Light from Electron Avalanches in Low Pressure TEA and TMAE Gas Mixtures, Nuclear Instruments and Methods A 275 (1989) 351 363.
Suzuki, M., et al., On the Optical Readout of Gas Avalanche Chambers and Its Applications, Nuclear Instruments and Methods in Physics Research A263 (1988) pp. 237-242.
Charpak, et al., Some Applications of the Imaging Proportional Chamber, presented at the IEEE Nuclear Science Symposium, San Francisco, 21-23 Oct. 1987, IEEE Transactions on Nuclear Science, NS-35, p. 483, (1988).

*Primary Examiner*—Carolyn E. Fields
*Attorney, Agent, or Firm*—Ladas & Parry

[57] ABSTRACT

Apparatus for digital imaging including at least one electron multiplier arranged to receive beta radiation from a sample, apparatus for collimating the beta radiation without totally blocking all radiation from any location within a given region of interest on the sample, and readout electrodes operative in response to electrons from the electron multiplier to provide a first output indication of the incidence and location of beta radiation from the sample.

15 Claims, 15 Drawing Sheets

APPARATUS FOR DIGITAL IMAGING

FIELD OF THE INVENTION

The present invention relates to biochemical, medical and biological analysis generally and more particularly to automated reading and digitization of radiation emitter tagged flat images.

BACKGROUND OF THE INVENTION

There exist various chemical and biological analysis techniques which employ radiation emitter tagging. One such technique is gel electrophoresis which produces a radiation tagged flat image having a multiplicity of lines on a gel, each line representing a molecular component of given characteristics.

Increasingly, for the purpose of research and clinical diagnostics it is desired to quantify the results obtained, such that computer analyses and operations can be applied thereto.

One existing technique is to contact print from the gel onto radiation sensitive film. This technique, known as autoradiography, is slow, due to the relatively low radiation intensity involved and can require days in order to obtain a useful result, which must then be digitized by the use of a densitometer.

There are also known apparatus and techniques for automated reading of tagged images, such as that exemplified in the Betascope 603 Blot Analyzer which is available from Betagen Corporation of 100 Beaver Street, Waltham MA 02154, U.S.A.

There is also known a radioanalytical imaging system which operates by scanning a sample with an ionization gas detector and provides resolution to at least 0.8 mm. Such a system is commercially available from AMBIS Systems of San Diego, Calif. 92123, U.S.A.

The AMBIS system employs a collimator which totally blocks all radiation from certain regions on the sample. Accordingly, in order that valuable and important information not be lost, the AMBIS system requires that the location of the sample be shifted repeatedly with respect to the collimator.

Automatic techniques for analysis of non-radioactive electrophoretic gels are also known. Apparatus and software employing such a technique is available from Pharmacia LKB Biotechnology AB, of Uppsala, Sweden under the trademarks UltroScan XL and GelScan XL.

Various types of multi-step radiation detectors are known in the detection art. Examples of papers in this area include the following:

The Multistep Avalanche Chamber for Beta Radiochromatography by Ariella Cattai, Nuclear Instruments and Methods in Physics Research 215 (1983) pp 489-492;

The Multistep Avalanche Chamber as a Detector in Radiochromatography Imaging, by G. Petersen et al, Nuclear Instruments and Methods 176 (1980) pp 239-244;

An Improved Multistep Avalanche Detector System for Digital Autoradiography, by J. E. Bateman, et al, Nuclear Instruments and Methods in Physics Research A264 (1988) pp 430-435;

The Multistep Avalanche Chamber, A New Family of Fast High Rate Particle Detectors, by A. Breskin et al, Nuclear Instruments and Methods 161 (1979), pp 19-34; and A multistep parallax-free X-ray Imaging Counter, A. Breskin, et al., Nuclear Instruments and Methods 195 (1982) pp 469-473.

A systematic study of the emission of light from electron avalanches in low pressure TEA and TMAE gas mixtures by D. Sauvage, A. Breskin and R. Chechik Nuclear Instruments and Methods A275, (1989) pp 351-363;

On the Optical Readout of Gas Avalanche Chambers and its Applications, by M. Suzuki, A. Breskin et al., Nuclear Instruments and Methods in Physics Research A263 (1988) pp 237-242;

Some Applications of the Imaging Proportional Chamber by G. Charpak, A. Breskin, R. Chechik et al, presented at the IEEE Nuclear Science Symposium, San Francisco, 21-23 October 1987, IEEE Transactions on Nuclear Science, NS-35, p 483 (1988);

SUMMARY OF THE INVENTION

The present invention seeks to provide an improved apparatus and technique for high resolution automatic analysis of radioactive images.

There is thus provided in accordance with a preferred embodiment of the present invention, apparatus for digital imaging including at least one electron multiplier arranged to receive beta radiation from a sample, apparatus for collimating the beta radiation without totally blocking all radiation from any location within a given region of interest on the sample, and readout electrodes operative in response to electrons from the electron multiplier to provide a first output indication of the incidence and location of beta radiation from the sample.

In accordance with a preferred embodiment of the present invention, the apparatus for collimating comprises a thin foil located intermediate the sample and the electron multiplier.

In accordance with another preferred embodiment of the invention, the apparatus for collimating is arranged downstream of the readout electronics and there is also provided coincidence sensing apparatus arranged downstream of the collimating apparatus for providing a second output indication of the incidence of electrons thereon corresponding to beta radiation having a predetermined angular distribution and ANDing apparatus for receiving the second output indication from the coincidence sensing apparatus and the first output indication from the readout electrodes for providing a third output indication representative of the location of beta radiation having the predetermined angular distribution.

Additionally in accordance with a preferred embodiment of the invention, the apparatus for digital imaging also comprises electronic readout apparatus for displaying the third output indication.

Further in accordance with a preferred embodiment of the invention, the apparatus for digital imaging also comprises apparatus disposed downstream of the coincidence sensing apparatus for providing a fourth output indication of the impingement thereon of cosmic radiation and NAND apparatus responsive to the fourth output indication for generally eliminating indications produced by cosmic radiation in the third output indication.

Further in accordance with an embodiment of the invention, the collimating apparatus includes an apertured plate. Alternatively it may comprise a solid plate of predetermined thickness. The collimating apparatus may be selectably variable and may include a selectably positionable collimator having different collimating characteristics at different locations thereon.

Additionally in accordance with a preferred embodiment of the invention, there is provided apparatus for digital imaging including at least one electron multiplier arranged to receive beta radiation from a sample, readout electrodes operative in response to electrons from the electron multiplier to provide a first output indication of the incidence and location of beta radiation from the sample, coincidence sensing apparatus arranged downstream of the electron multiplier for providing a second output indication of the incidence of beta radiation thereon and ANDing apparatus for receiving the second output indication from the coincidence sensing apparatus and the first output indication from the readout electrodes for providing a third output indication representative of the location of beta radiation generally free of spurious indications produced by "hot spots", i.e. spontaneous emissions of electrons at the entrance region of the electron multiplier.

Additionally in accordance with a preferred embodiment of the invention, the electron multiplier comprises apparatus for collimating the beta radiation without totally blocking all radiation from any location within a given region of interest on the sample, a light amplification region providing a multiple photon output indicative of the path of the emitted radiation through the electron multiplier, image intensification apparatus receiving the photon output of the avalanche chamber, a camera receiving an output from the image intensification apparatus; image processing apparatus for receiving the camera output.

Further in accordance with a preferred embodiment of the invention, the camera comprises a CCD camera or any other suitable imaging device.

Additionally in accordance with a preferred embodiment of the invention, the electron multiplier comprises a plurality of gas-filled regions separated from each other by wire grids.

BRIEF DESCRIPTION OF THE DRAWINGS

The present invention will be understood and appreciated more fully from the following detailed description, taken in conjunction with the drawings in which.

DETAILED DESCRIPTION OF A PREFERRED EMBODIMENT

Figure 1:
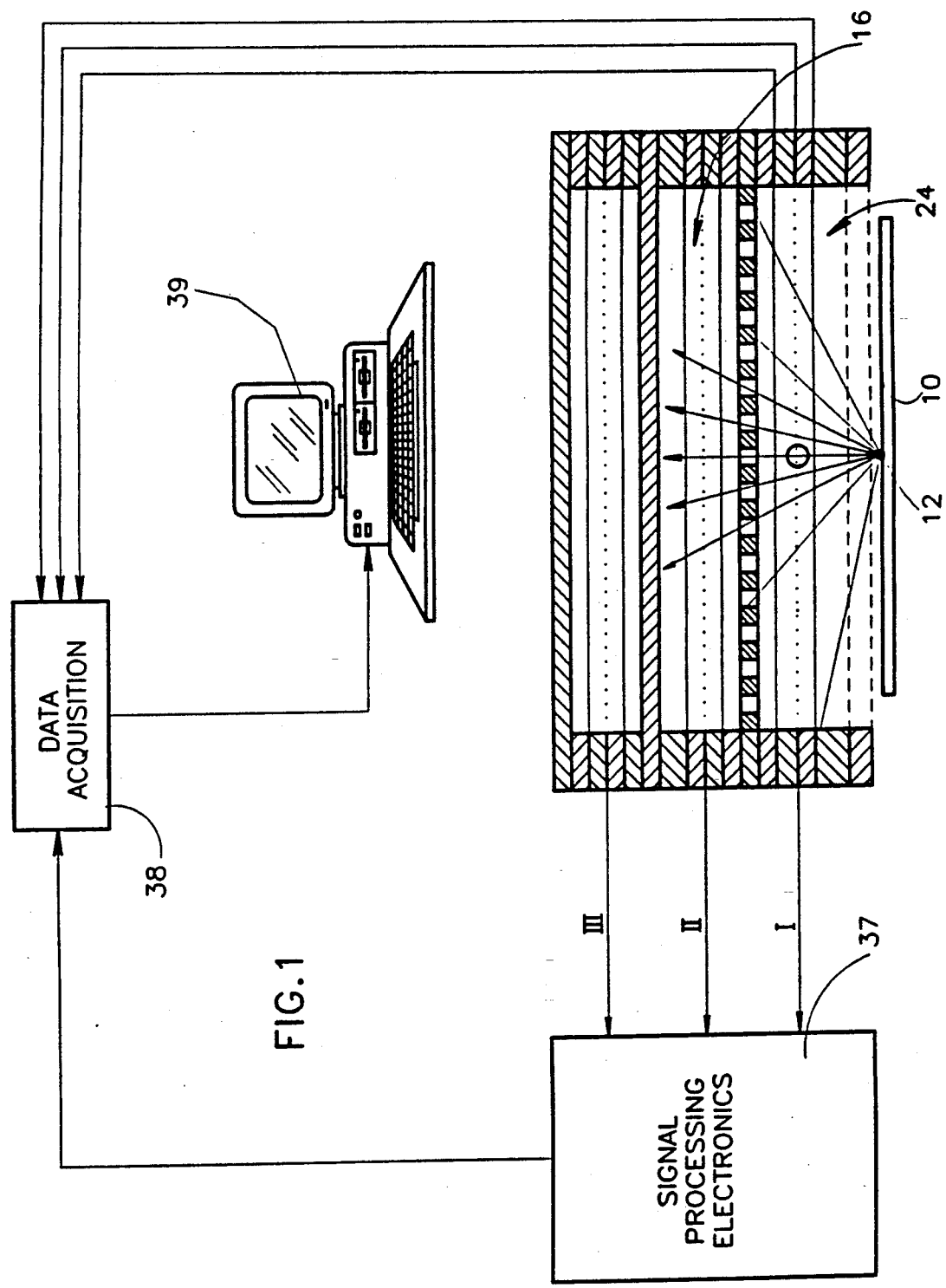
FIG. 1 is a schematic illustration of apparatus for high resolution automatic analysis of radioactive images constructed and operative in accordance with a preferred embodiment of the present invention.
Figure 2:
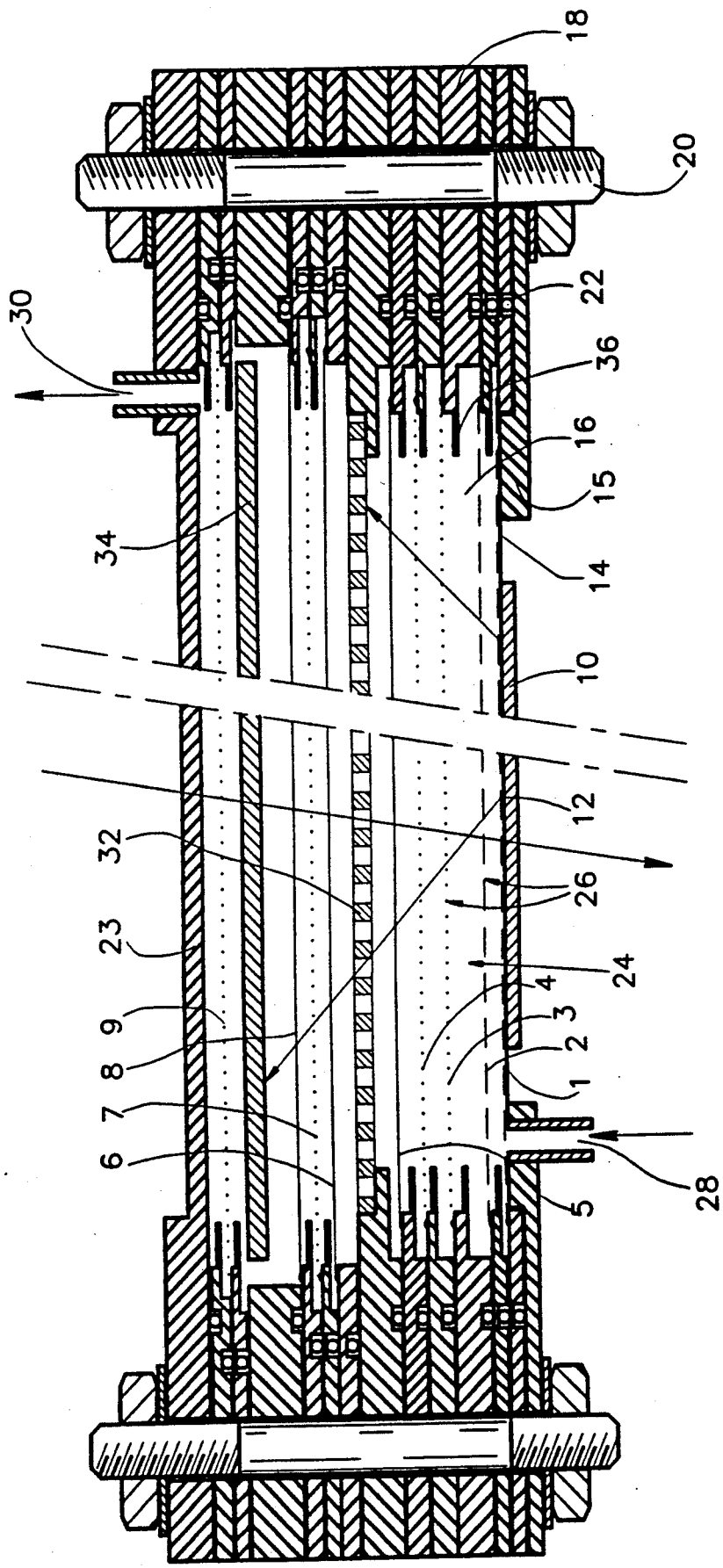
FIG. 2 is a side sectional illustration of an avalanche chamber constructed and operative in accordance with a preferred embodiment of the present invention and forming part of the apparatus of FIG. 1.

Reference is now made to FIGS. 1 and 2, which illustrate apparatus for high resolution automatic analysis of radioactive images constructed and operative in accordance with a preferred embodiment of the present invention. The apparatus includes a support 10 onto which a thin generally flat sample 12 is placed. The sample is typically a beta-labeled gel or a thin biological sample.

Beta radiation emitted by the sample 12 passes through a thin window 14 (FIG. 2), typically formed of Mylar of thickness 0.5-25 microns, into an electron multiplier 16. In the case of samples which produce very low energy beta electrons, such as beta electrons from tritium, the sample may be placed inside the gas volume of the electron multiplier. Electron multiplier 16 is preferably constructed as will be described hereinafter in detail with additional reference to FIGS. 3, 4 and 5. As it passes through the electron multiplier 16, the beta radiation produces a series of avalanches of electrons.

Reference is now made particularly to FIG. 2, which illustrates a preferred embodiment of the electron multiplier employed in the present invention. The electron multiplier 16 comprises a plurality of peripheral frame members 18, which are made of an insulating material such as G-10 epoxy laminate and are joined together by transverse bolts 20 which compress O-rings 22 to define together with a electrically conductive back cover 23 and a front cover 15, including window 14, a gas tight enclosure 24.

The gas tight enclosure is divided into a plurality of generally planar regions by a plurality of mesh or parallel wire electrodes 26 of conventional arrangement and construction which are supported between adjacent frame members 18 in generally parallel spaced orientation.

For convenience in future reference, the electrodes are numbered in the illustration from 1 to 9. A gas inlet 28 and gas outlet 30 are defined in association with the gas tight enclosure 24.

Typically, the enclosure 24 is filled with a gas mixture of about 93% argon and 7% propane.

The electron multiplier may be operated in a mode wherein the voltages of the various electrodes 26 are as follows:

| Electrode # | Voltage (Volts) |
| --- | --- |
| 9 | +1600 |
| 8 | 0 |
| 7 | +1600 |
| 6 | 0 |
| 5 | 0 |
| 4 | +2750 |
| 3 | 0 |
| 2 | −500 |
| 1 | −4500 |

Figure 6B:
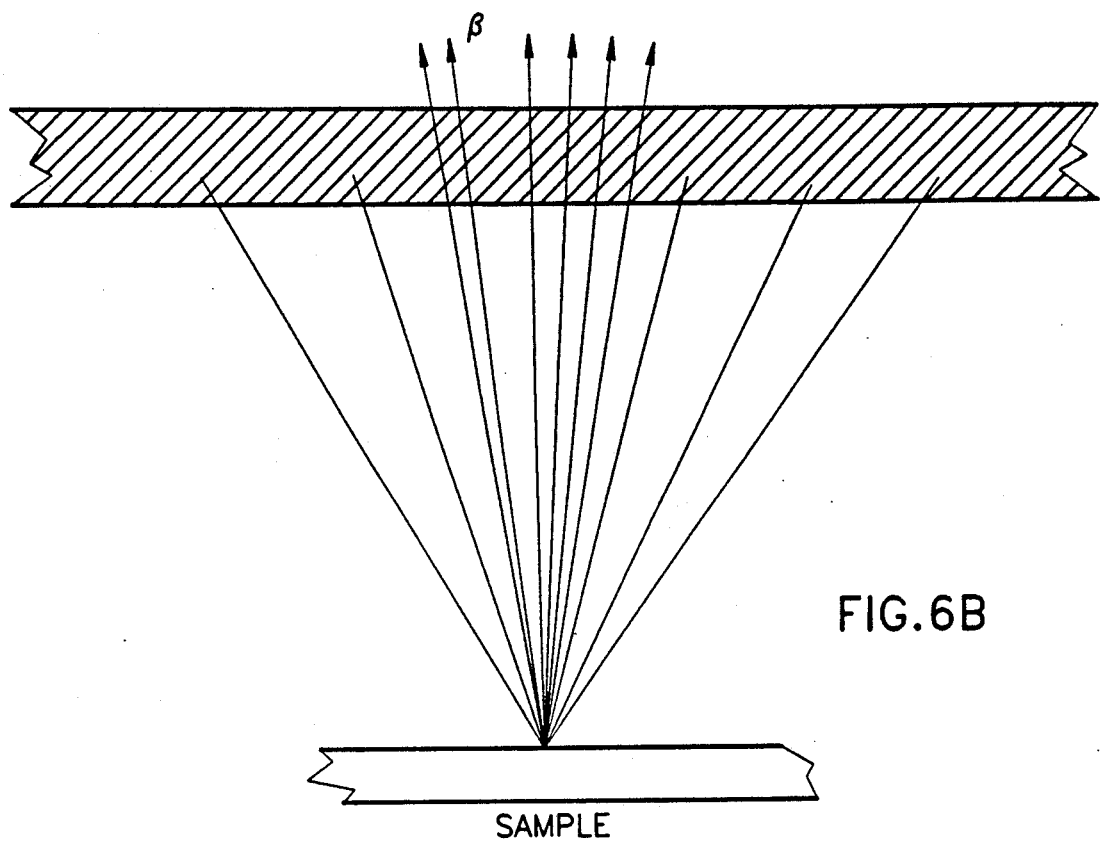
FIGS. 6A and 6B illustrate the operation of two different types of collimation apparatus useful in the present invention.
Figure 6A:
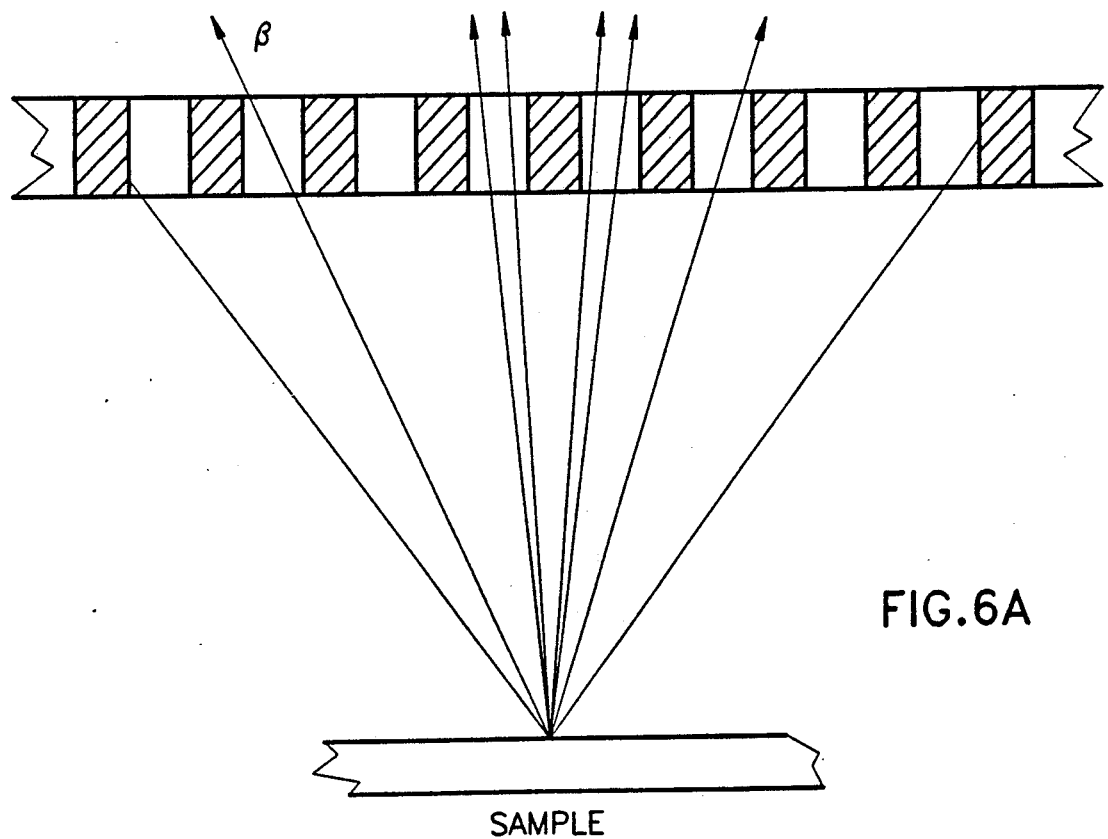

Preferably electrodes 1, 2, 6 and 8 are mesh electrodes, which may be of the construction illustrated in FIG. 6A. The mesh electrodes are preferably formed of wires of stainless steel having a diameter of 20-100 microns. The wires are preferably spaced from each other (center to center) by about between 200-500 microns. The mesh is commercially available from G. Bopp & Co. A. G. of Zurich, Switzerland.

Figure 7A:
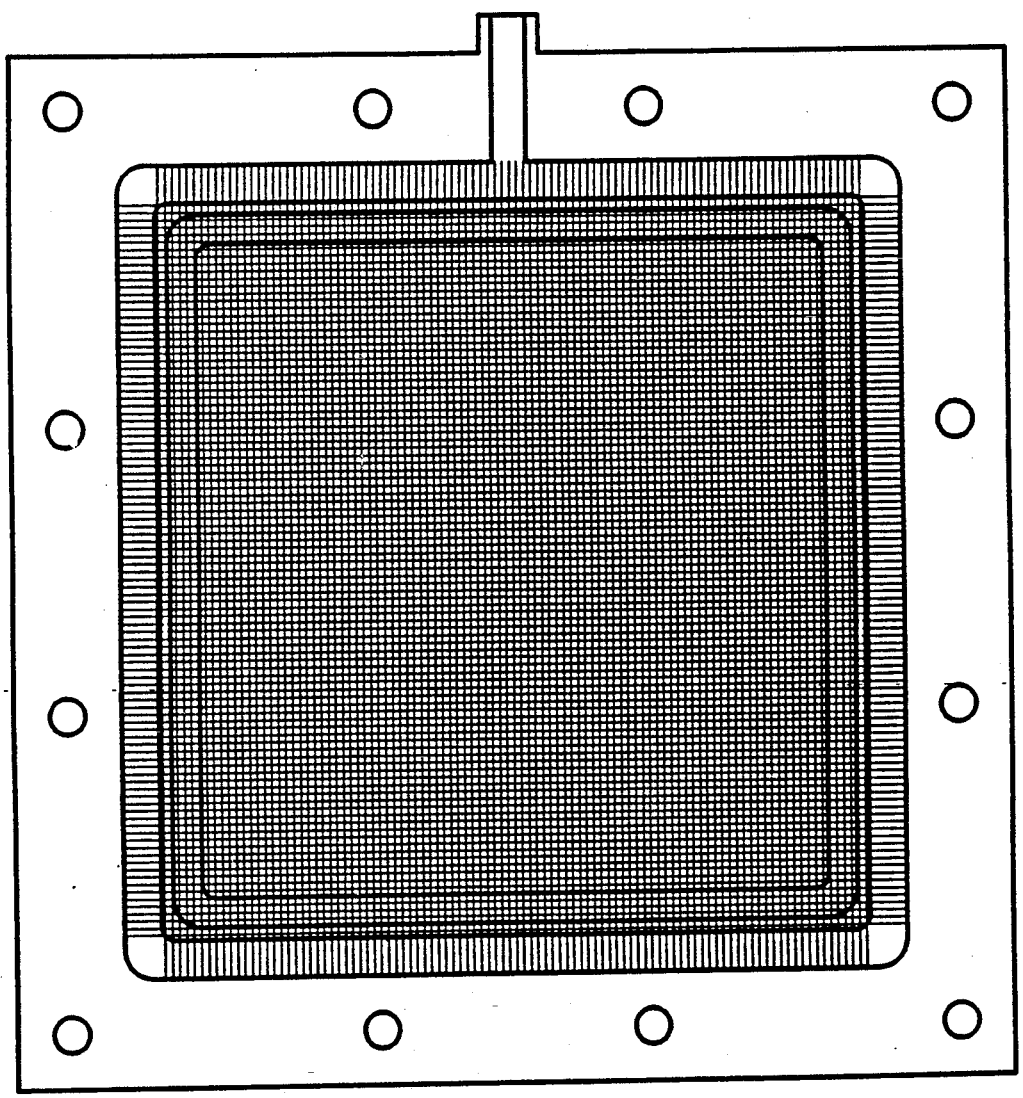
FIGS. 7A, 7B and 7C are planar illustrations of various embodiments of electrode assemblies useful in the apparatus of FIGS. 1-5.
Figure 7B:
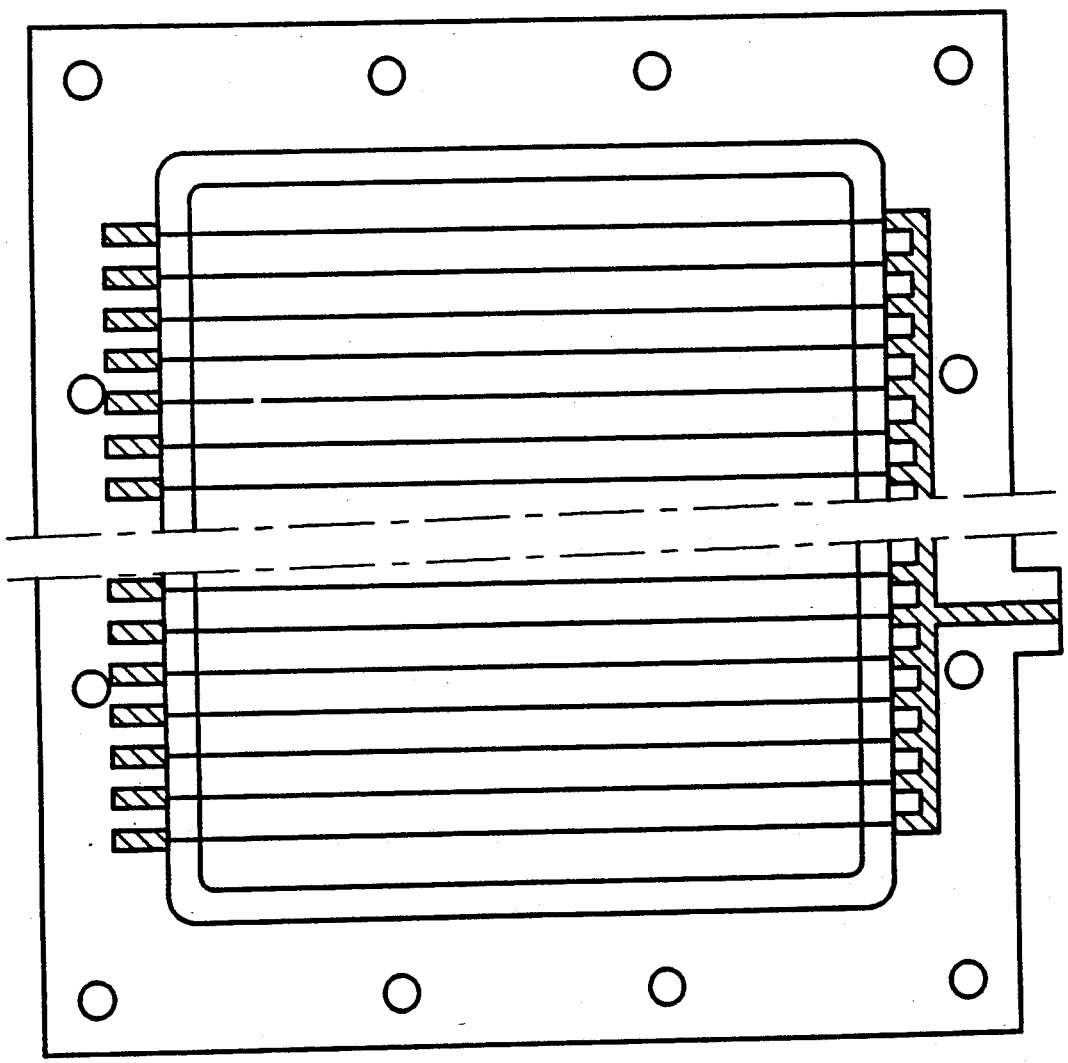
Figure 7C:
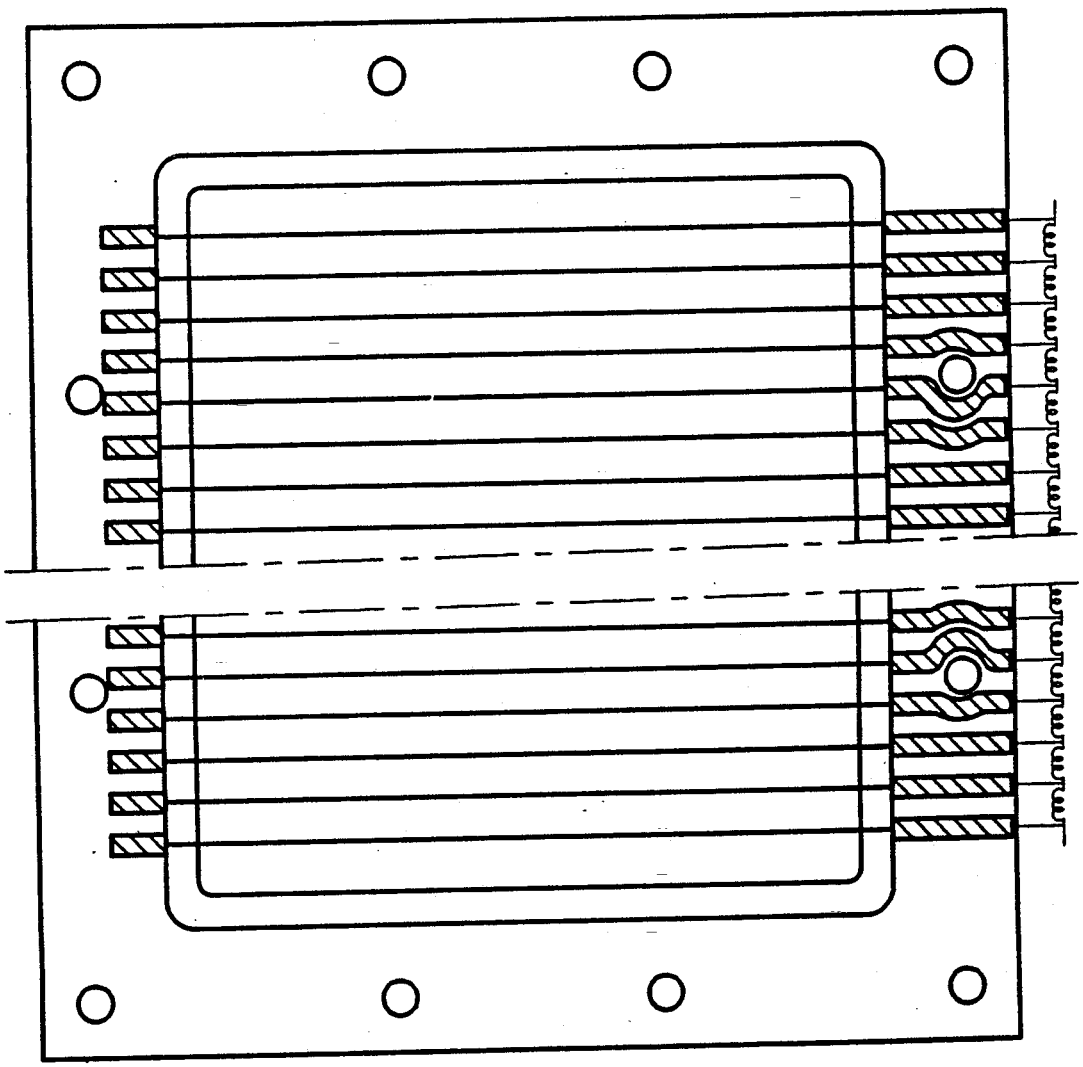

Preferably electrodes 4, 7 and 9 are parallel wire electrodes of the construction illustrated in FIG. 7B. Preferably electrodes 3 and 5 are parallel wire electrodes having associated delay lines, as illustrated in FIG. 7C and are arranged such that their wires lie in relative perpendicular orientations in mutually parallel planes. The wires employed in the parallel wire electrodes are commercially available from Lumametall AB of Kalmar, Sweden. The delay lines are commercially available from Pulse Engineering, a division of Varian, of San Diego, Calif. under catalog number 21171.

Preferably electrodes 1 and 2 are formed with parallel wires in each direction separated by no more than 200 microns.

Preferably the inter-wire separations and wire thickness of the parallel wire electrodes are as follows:

| Electrode Number | Wire thickness (microns) | Inter-wire separation (mm) |
| --- | --- | --- |
| 9 | 20 | 5 |
| 7 | 20 | 5 |
| 5 | 50 | 1 |
| 4 | 20 | 1 |
| 3 | 50 | 1 |

In accordance with a preferred embodiment of the invention there is disposed between electrodes 5 and 6 a collimator plate 32, preferably as illustrated in either of FIGS. 6A and 6B. Additionally, between electrodes 8 and 9 there is provided an absorber plate 34, typically formed of stainless steel of thickness 0.5-2 mm.

Preferably, for the voltage stated hereinabove, the separations between adjacent electrodes and between the electrodes and other elements of the electron multiplier, along a direction perpendicular to their respective planes, are 3 mm except for the separation between electrodes 2 and 3, which is between 8 and 10 mm.

The embodiment of FIG. 2 also includes a structure for field shaping at the periphery of the avalanche gaps. This structure comprises thin peripheral extensions 36 of the insulator between each wire plane. This structure provides enhanced shaping of the electric field and thus prevents spontaneous sparking at the periphery.

Beta electrons from the sample 12 penetrate through window 14 and are operative to ionize the gas mixture within enclosure 24. Electrons produced by the ionization in the region between electrodes 1 and 2 are multiplied by the electric field produced by electrodes 1 and 2, producing an electron avalanche.

A part of the electrons in the avalanche passes through mesh electrode 2 through a transfer region defined between electrodes 2 and 3 and enter an electron multiplier defined by electrodes 3, 4 and 5. These electrons drift towards electrode 4 and are multiplied in the vicinity of the thin wires defining electrode 4.

During this second multiplication charges are induced on electrodes 3, 4 and 5, producing induced electrical signals on electrodes 3, 4 and 5 which indicate the presence and location of the original beta electron emissions. The electrical signals on electrode 4 indicate the presence of the beta electron emissions, while the electrical signals on electrodes 3 and 5 indicate their location, with the use of the delay lines illustrated in FIG. 7C. Indication of the location is conventional, as described in The Multistep Avalanche Chamber for Beta Radiochromatography by Ariella Cattai, Nuclear Instruments and Methods in Physics Research 215 (1983) 489–492, the disclosure of which is hereby incorporated by reference.

The original beta electrons emitted by the sample 12 impinge upon a collimator 32. Those beta electrons which are within a predetermined selected non-isotropic angular distribution pass through the collimator 32. These beta electrons ionize the gas mixture within enclosure 24 in the region of electrodes 6, 7 and 8, which define an electron multiplier functioning as a coincidence detector.

Electrons produced in the coincidence detector are collected at electrode 7 and produce an avalanche which provides an electrical signal on electrode 7, indicating the presence of such beta electrons. Coincidence between the outputs of electrode 7 and electrode 4 enables beta radiation falling within the selected angular distribution to be distinguished from other beta radiation and electrical noise.

The beta electrons emitted by sample 12 which were not earlier absorbed are stopped by absorber plate 34. An anticoincidence detector is defined by absorber plate 34, back cover 23 and electrode 9 disposed therebetween. Absorber plate 34 and cover 23 are preferably grounded. Ionization electrons producing an electrical signal on electrode 9 indicate the presence of ionizing radiation such as cosmic rays and enable such radiation, which normally is also detected by the other electron multipliers, to be disregarded. Returning now to FIG. 1, three outputs are provided by electron multiplier 16. Output I represents the electrical signals along electrode 4, output II represents the electrical signals along electrode 7 and output III represents the electrical signals along electrode 9. Outputs I, II and III are supplied to signal processing electronics 37 which outputs to data acquisition circuitry 38 associated with a computer workstation 39. Signal processing electronics 37 and acquisition circuitry 38 are illustrated in detail in FIG. 8, and will be described hereinbelow in detail.

Figure 3:
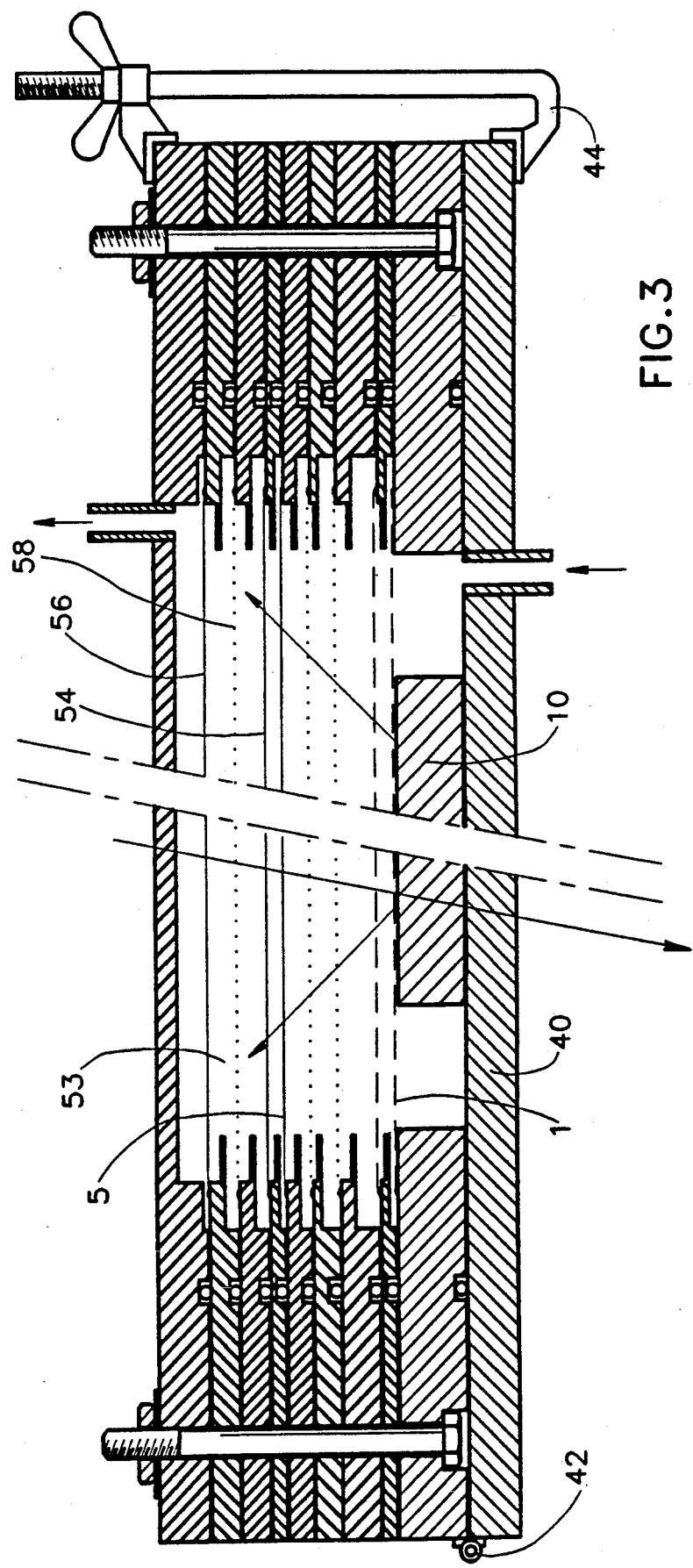
FIG. 3 is a side sectional illustration of an avalanche chamber constructed and operative in accordance with another preferred embodiment of the present invention and forming part of the apparatus of FIG. 1.

Reference is now made to FIG. 3, which illustrates an alternative preferred embodiment of avalanche chamber constructed and operative in accordance with the present invention. The avalanche chamber of FIG. 3 is similar to that shown in FIG. 2, with the following differences:

Window 14 of the embodiment of FIG. 2 is eliminated and instead, a front panel 40 of the electron multiplier is pivotably mounted onto the remainder of the electron multiplier by means of a hinge 42 and is locked in place by means of a threaded locking bracket 44. A sample bearing sample support 10 may be placed directly against electrode 1.

In this embodiment, the collimator is eliminated and the coincidence detector 53 is incorporated into the avalanche chamber downstream of the mesh electrode which is identified by index 5. The coincidence detector is preferably in the form of a multi-wire proportional counter and comprises first and second wire cathode planes 54 and 56, the wires of which extend mutually perpendicularly, as shown. The wires are typically of diameter 50 microns and are spaced from each other (center to center) by about 5 mm.

The coincidence detector 53 also comprises an anode wire plane 58, formed of relatively thin wires, typically having a 20 micron diameter, which wires are spaced from each other by 1 mm.

The provision of coincidence detector 53 in the avalanche chamber ensures that only beta particles having a given minimum range are measured, inasmuch as particles, such as spontaneous emission electrons, having a shorter range, do not actuate the coincidence detector 53, which may be used for gating purposes.

The voltages on the wire planes 54, 58 and 56 are indicated by indices 6, 7 and 8 and are as follows, when the indices 1-5 are defined as stated hereinabove:

| Electrode # | Voltage (Volts) |
| --- | --- |
| 8 | 0 |
| 7 | +1600 |
| 6 | 0 |

Figure 4:
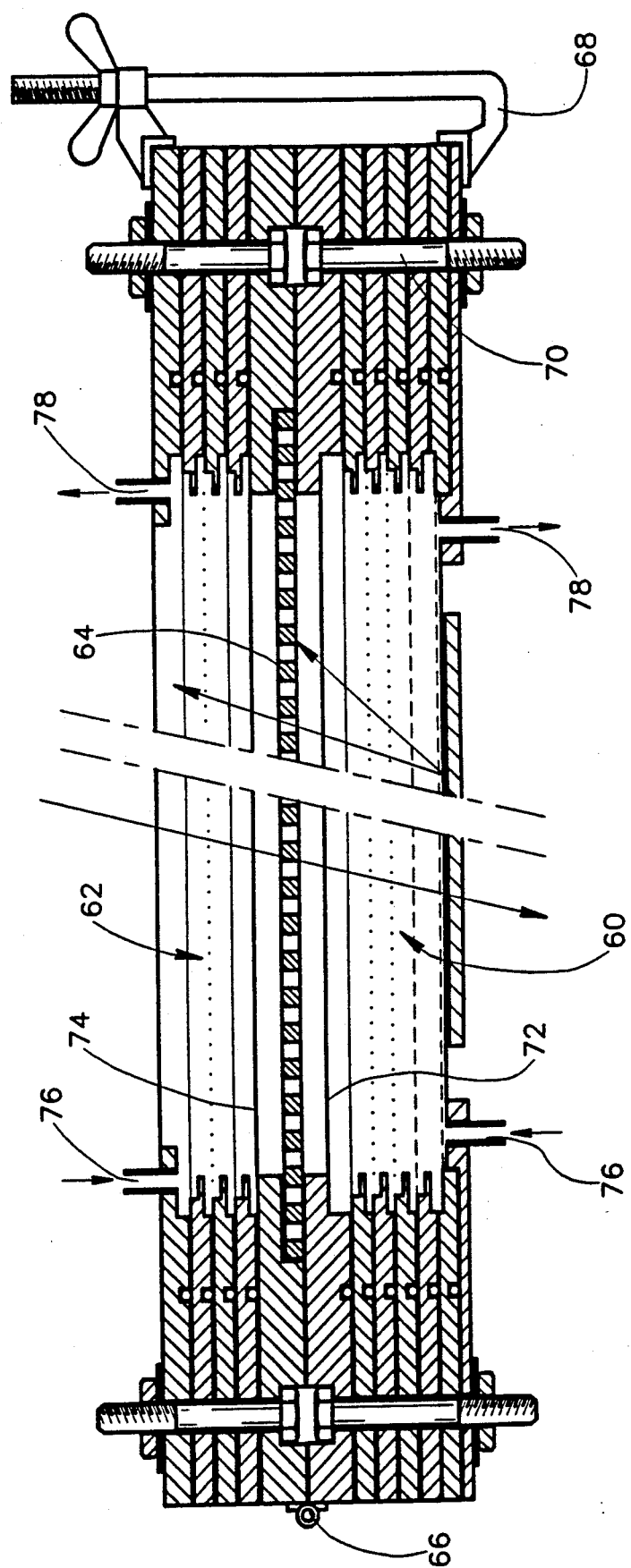
FIG. 4 is a side sectional illustration of an avalanche chamber constructed and operative in accordance with yet another preferred embodiment of the present invention and forming part of the apparatus of FIG. 1.

Reference is now made to FIG. 4, which illustrates an avalanche chamber constructed and operative in accordance with another embodiment of the invention wherein two separate gas enclosures 60 and 62 are defined and separated by a collimator 64. The overall structure is similar to that of the embodiment of FIG. 2, with changes as described hereinbelow.

In contrast to the structure of FIG. 2, here the two gas enclosures 60 and 62 are hinged together by means of a hinge 66 and clamped together by means of a clamp 68. Each of the enclosures 60 and 62 is held together by bolts 70. The enclosures 60 and 62 taken together comprise all of the electrodes in the embodiment of FIG. 3. Additionally each of the enclosures 60 and 62 includes a foil disposed adjacent the collimator 64. These foils, indicated by reference numerals 72 and 74 respectively provide gas sealing of the enclosures 60 and 62, and a typically formed of Mylar, a trademark of DuPont for polyethylene terephthalates of thickness 6-15 microns, in order to allow beta radiation to freely pass therethrough.

Each of enclosures 60 and 62 is provided with a respective gas inlet and gas outlet, indicated by reference numerals 76 and 78.

The structure of the embodiment of FIG. 4 enables the collimator 64 to be readily removed and replaced so as to enable the operator to choose levels of efficiency and resolution that best suit his objectives.

Figure 5:
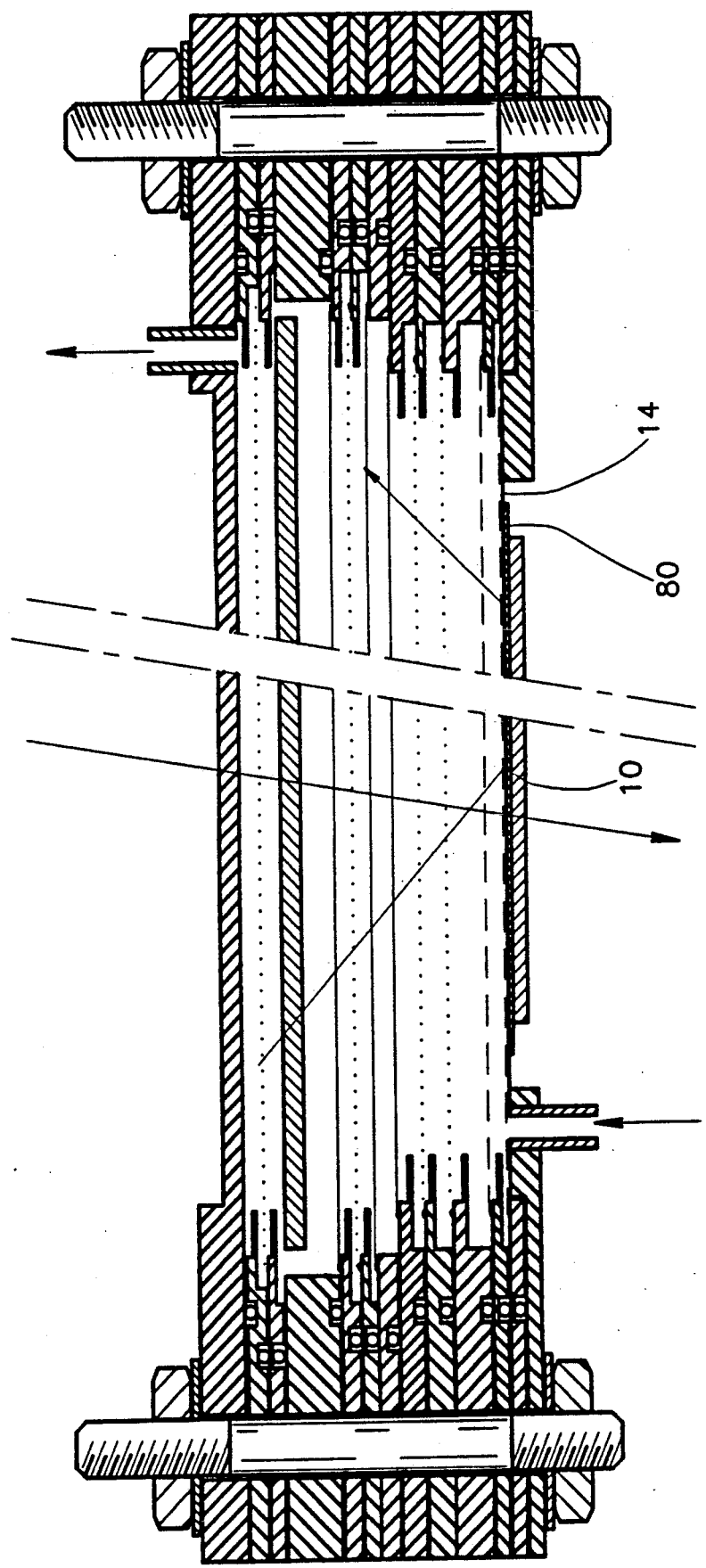
FIG. 5 is a side sectional illustration of an avalanche chamber constructed and operative in accordance with still another preferred embodiment of the present invention and forming part of apparatus similar to the apparatus of FIG. 1.

Reference is now made to FIG. 5, which illustrates an avalanche chamber constructed and operative in accordance with another embodiment of the invention similar to that of FIG. 2 but wherein collimator 32 is replaced by a collimating foil 80 disposed immediately adjacent the sample 12 and between the sample and the window 14.

Figure 13B:
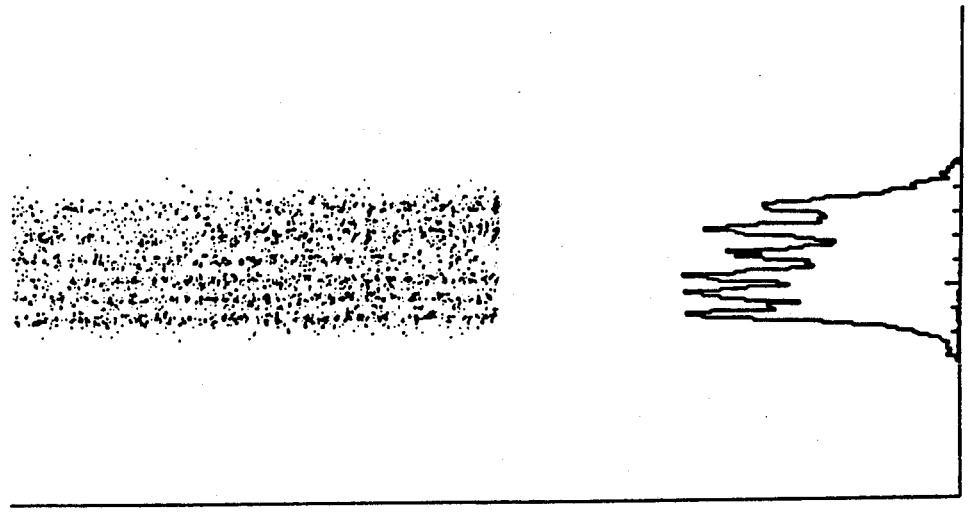
FIGS. 13A and 13B illustrate imaging resolution of a sample carried out with the apparatus of FIG. 5.
Figure 13A:
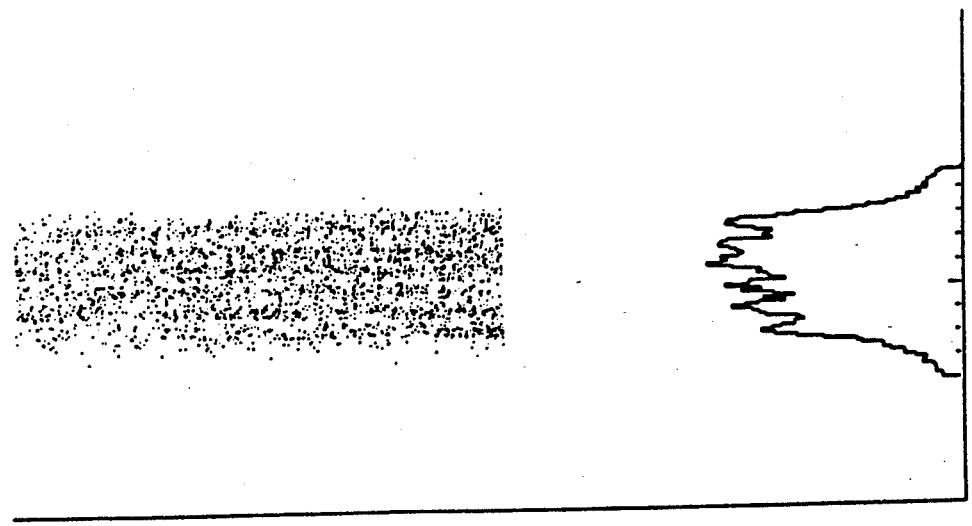

Collimating foil 80 is typically formed of tungsten of thickness 0.05-0.1 mm and is operative to pass beta electrons which are within a predetermined selected non-isotropic angular distribution. The use of a solid foil 80 as opposed to a perforated plate as employed in the prior art enables radiation from the entire sample to be detected without requiring lateral movement of the sample relative to the avalanche chamber. An illustration of the improved imaging resolution obtainable with such apparatus is provided in FIG. 13. A sample containing 6 $^{32}P$ labelled parallel lines, 1 mm apart, is arranged with a beta detector without (a) and with (b) a collimation arrangement as shown in FIG. 5. The improved line separation involves a relatively small loss of efficiency of 44% in this case.

FIGS. 6A and 6B respectively illustrate the operation of perforated plate collimator 32 in the embodiment of FIG. 2, for example, and of foil collimator 80 in the embodiment of FIG. 5. It is appreciated that a foil type collimator may be used in the embodiment of FIG. 4.

Figure 8:
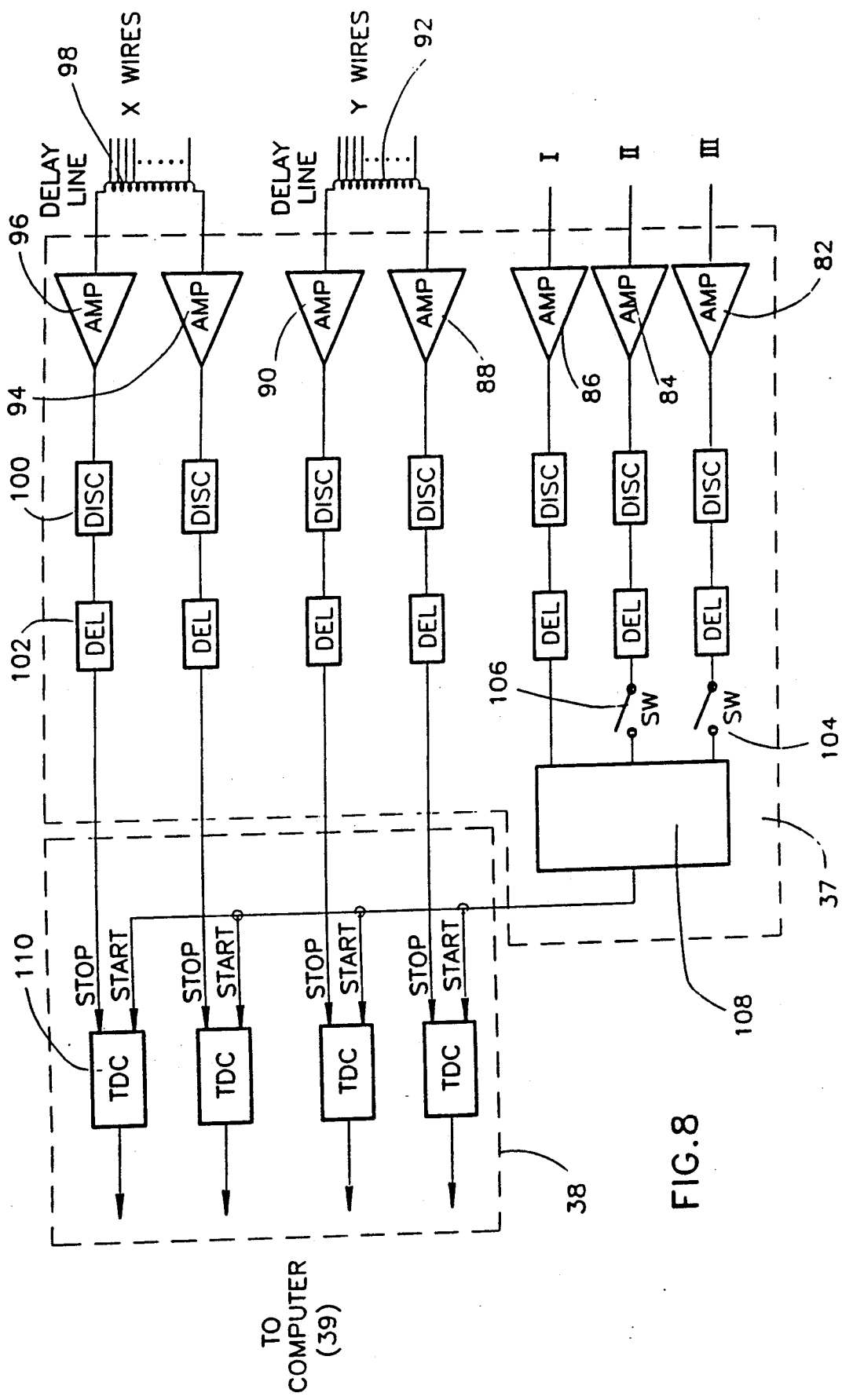
FIG. 8 is a schematic illustration of electronic apparatus forming part of the system of FIG. 1.

Reference is now made to FIG. 8, which illustrates in more detail the signal processing electronics 37 and the data acquisition circuitry 38 of FIG. 1. The signal processing electronics 37 comprises a plurality of amplifiers 82, 84 and 86 which receive respective inputs I, II and III, corresponding respectively to electrodes 4, 7 and 9 in the embodiment of FIG. 2, each having the structure illustrated in FIG. 7B.

Additional amplifiers 88 and 90 receive inputs from the Y-wires of electrode 3 in the embodiment of FIG. 2 via a conventional delay line 92. Additional amplifiers 94 and 96 receive inputs from the X-wires of electrode 5 in the embodiment of FIG. 2 via a conventional delay line 98.

The outputs of all of amplifiers 82, 84, 86, 88, 90, 94 and 96, which are all typically model LeCroy Model TRa 1000, are each supplied to a discriminator 100, such as a ORTEC Quad CFD 934, commercially available from ORTEC of Oak Ridge, Tenn., U.S.A. The outputs of each discriminator 100 are supplied to a delay line 102, typically comprising a 50 ohm coaxial cable.

The outputs of the delay lines 102 carrying the outputs from amplifiers 82 and 84 are suppled via respective switches 104 and 106 to a selectable AND/NAND circuit 108, such as an ESN CO4000, commercially available from ORTEC of Oak Ridge, Tenn., which also receives the output of the delay line 102, carrying the output from amplifier 86.

Data acquisition circuitry 38 comprises four time-to-digital converters 110, such as Model 2228A from Lecroy Research Systems of Spring Valley, N.Y., U.S.A. The START inputs to each of converters 110 are supplied by the output of AND/NAND circuit 108, while the STOP inputs are supplied by respective outputs of delay lines 102 carrying the outputs of amplifiers 88, 90, 94 and 96. Converters 110 are located within a Camac crate and interface with computer 39 via an interface such as a P-Cam. The Camac crate and the P-Cam interface are commercially available from Kinetic Systems Corporation of Lockport, Ill., U.S.A.

Figure 9:
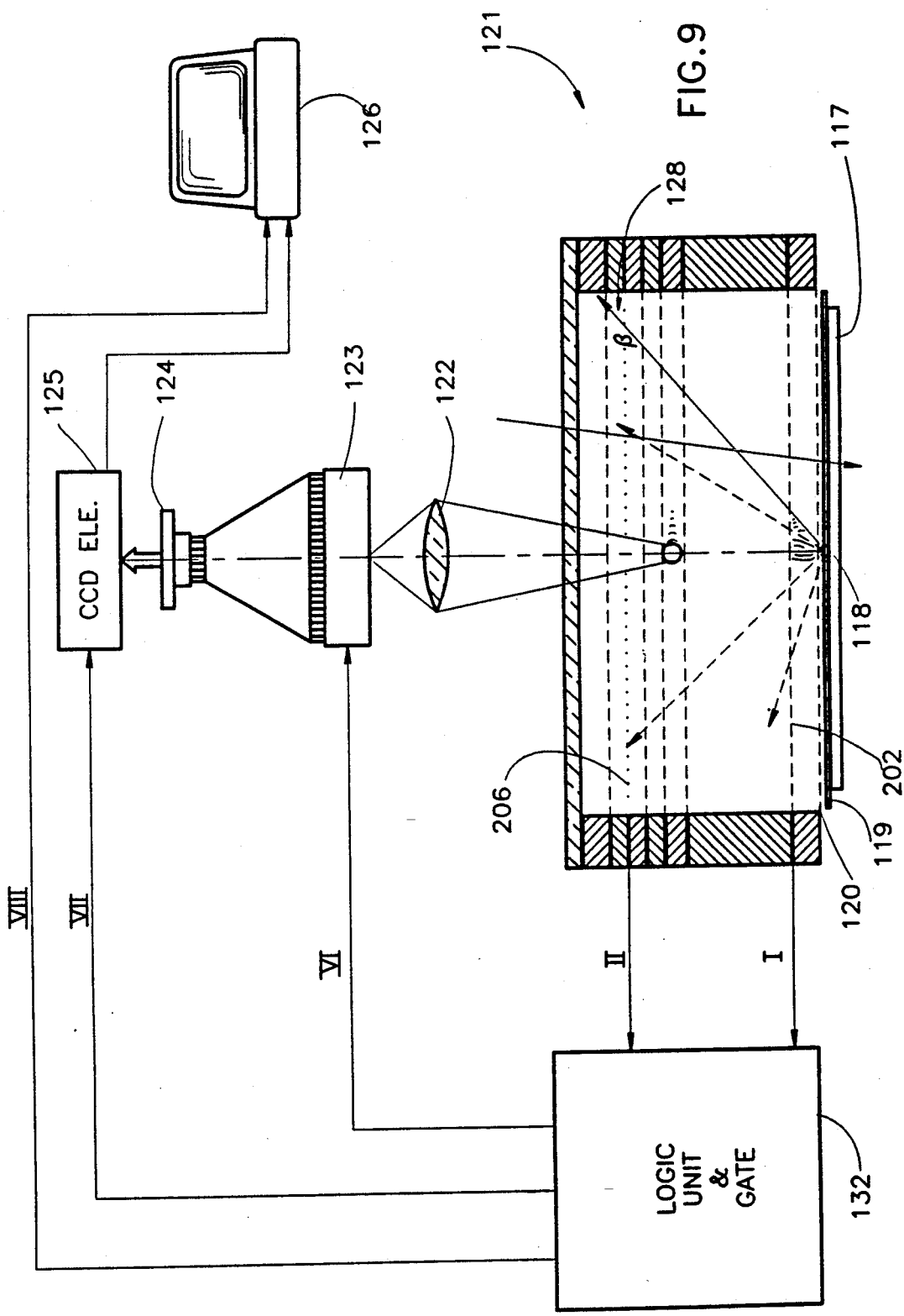
FIG. 9 is a schematic illustration of apparatus for high resolution automatic analysis of radioactive images constructed and operative in accordance with another preferred embodiment of the present invention including a coincidence detector, an absorber collimator and associated gating apparatus.
Figure 10:
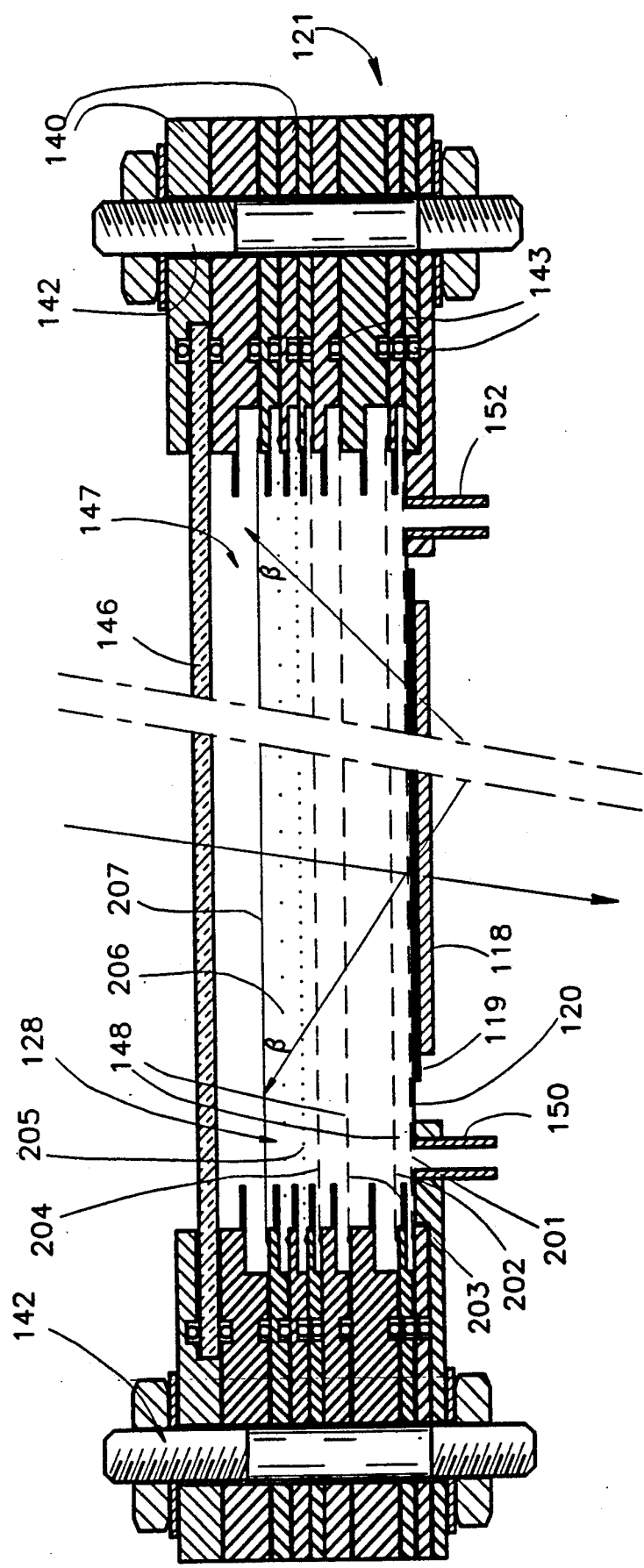
FIG. 10 is a side sectional illustration of an avalanche chamber constructed and operative in accordance with another preferred embodiment of the present invention and forming a part of the apparatus of FIG. 9.

Reference is now made to FIGS. 9 and 10, which illustrate apparatus for high resolution automatic analysis of radioactive images constructed and operative in accordance with a preferred embodiment of the present invention and employing electrooptical readout apparatus. The apparatus includes a stationary or movable support 117 onto which a thin sample 118 is placed. The sample is typically a beta-labeled gel or a thin biological sample.

Beta radiation emitted by the sample 118 passes through an absorber collimator foil 119, typically tungsten of a thickness of 0.05 mm, and a thin window 120, typically formed of Mylar of thickness 0.5–25 microns, into an avalanche chamber 121. Avalanche chamber 121 is preferably constructed as will be described hereinafter in detail with reference to FIG. 10.

As it passes through the avalanche chamber 121, the beta radiation produces a series of avalanches of electrons. By suitable choice of the gas filling avalanche chamber 121, an amount of photons, generally similar in quantity to the amount of electrons, is produced during the electron avalanche. This phenomenon is described in the abovementioned reference "On the Optical Readout of Gas Avalanche Chambers and its Applications" by M. Suzuki, A. Breskin et al., Nuclear Instruments and Methods in Physics Research A263 (1988) 237–242, the disclosure of which is hereby incorporated by reference.

The photon emissions from the avalanche chamber 121, produced by the beta emissions of the sample 118, are collected by a lens 122, such as a Lyman Alpha II, available from the Nye Optical Company of Troy Street, Spring Valley, Calif. 92072, and supplied to an image intensifier 123. A preferred image intensifier is a second generation fast gateable image intensifier such as a Proxitronic BV 2512QX having a 25 mm diameter S20 photocathode, and R 10 phosphor available from Proxitronic of Bensheim, W. Germany.

A CCD camera 124, such as a Thomson 7864FO 288×550 pixels 11 mm diagonal, receives the output of the image intensifier 123 and provides a video output to a frame grabber and digitizer 125, such as a Data Translation DT 2851, available from Data Translation of Marlboro, Mass., U.S.A.

The output of digitizer 125 is supplied to a computer 126 such as an IBM PC/AT, which displays the output of the digitizer.

In addition there is provided a coincidence detector 130 of the type described above in connection with FIGS. 2–5.

As seen in FIG. 9, a logic unit and gate circuit 132 receives gating signals I and II from the electrodes of the avalanche chamber, indicated by indices 202 and 206 via a suitable DC decoupler. The circuit 132 provides gating outputs to one or more of the following components of the system:

Output VI to image intensifier 123;
Output VII to the CCD electronics 125; and
Output VIII to the computer 126.

Reference is now made particularly to FIG. 10, which illustrates a preferred embodiment of the avalanche chamber employed in the present invention. The avalanche chamber comprises a plurality of peripheral frame members 140, which are made of an insulating material such as G-50 and are joined together by transverse bolts 142 which compress O-rings 143 to define together with window 120 and an optical window 146 a gas tight enclosure 147.

The gas tight enclosure is divided into a plurality of generally planar regions by a plurality of mesh or wire electrodes 148 which may be identical to the electrodes illustrated in FIGS. 7A and 7B and described hereinabove in connection therewith and with FIGS. 2–5.

For convenience in future reference, the electrodes are numbered in the illustration from 201 to 207. A gas inlet 150 and a gas outlet 152 are defined in association with window 120.

Typically, the enclosure 147 is filled with a gas mixture of about 90% argon, 5% methane and 5% triethylamine.

The avalanche chamber may be operated in a DC mode wherein the voltages of the various mesh electrodes 148 are as follows:

| Electrode # | Voltage (Volts) |
|---|---|
| 207 | 0 |
| 206 | +1700 |
| 205 | 0 |
| 204 | +5500 |
| 203 | +550 |
| 202 | 0 |
| 201 | −2700 |

Preferably electrodes 201–205 and 207 are mesh electrodes of the construction illustrated in FIG. 7A. Preferably electrode 206 is a parallel wire electrode, as illustrated in FIG. 7B.

Preferably electrode 206 is formed with parallel wires separated by 5 mm and a wire thickness of 20 microns.

Preferably the inter-wire separations and wire thickness of the mesh electrodes are as follows:

| Electrode Number | Wire thickness (microns) | Inter-wire separation (mm) |
|---|---|---|
| 207 | 50 | 0.5 |
| 205 | 50 | 0.5 |
| 204 | 50 | 0.5 |
| 203 | 50 | 0.5 |
| 202 | 63 | 0.2 |
| 201 | 63 | 0.2 |

The separations between adjacent electrodes are typically as follows

| Separation between Electrode Numbers | Distance (mm) |
|---|---|
| 207–206 | 3 |
| 206–205 | 3 |
| 205–204 | 15 |
| 204–203 | 5 |
| 203–202 | 10 |
| 202–201 | 3 |

A coincidence detector 128 is incorporated into the avalanche chamber downstream of the mesh electrode which is identified by index 204 and includes electrodes 205, 206 and 207. The structure of the coincidence detector is similar to that shown in FIG. 2 and described hereinabove in connection therewith.

The operation of the apparatus of FIG. 10 may be summarized as follows: beta particles emitted from sample 118 pass through absorber collimator 119, which determines their angular distribution. Downstream thereof, the beta particles which are not absorbed by collimator 119 pass through window 120 and ionize a gas in the region between electrodes 201 and 202.

The ionized gas produces an avalanche of electrodes in the direction of electrode 202. Some of the resulting electrons enter the region between electrodes 202 and 203 and drift towards electrode 203 and pass through electrode 203. In the region between electrodes 203 and 204, the electric field is selected such that the ionized gas emits UV photons.

As noted in connection with FIG. 9, the UV photons are received via a lens 122 and an image intensifier 123 and are imaged by a CCD camera 124.

Coincidence detector 128 is employed in this embodiment to eliminate spurious effects of spontaneous emission of electrons from electrode 201 and window 120, i.e. "hot spots".

Figure 11:
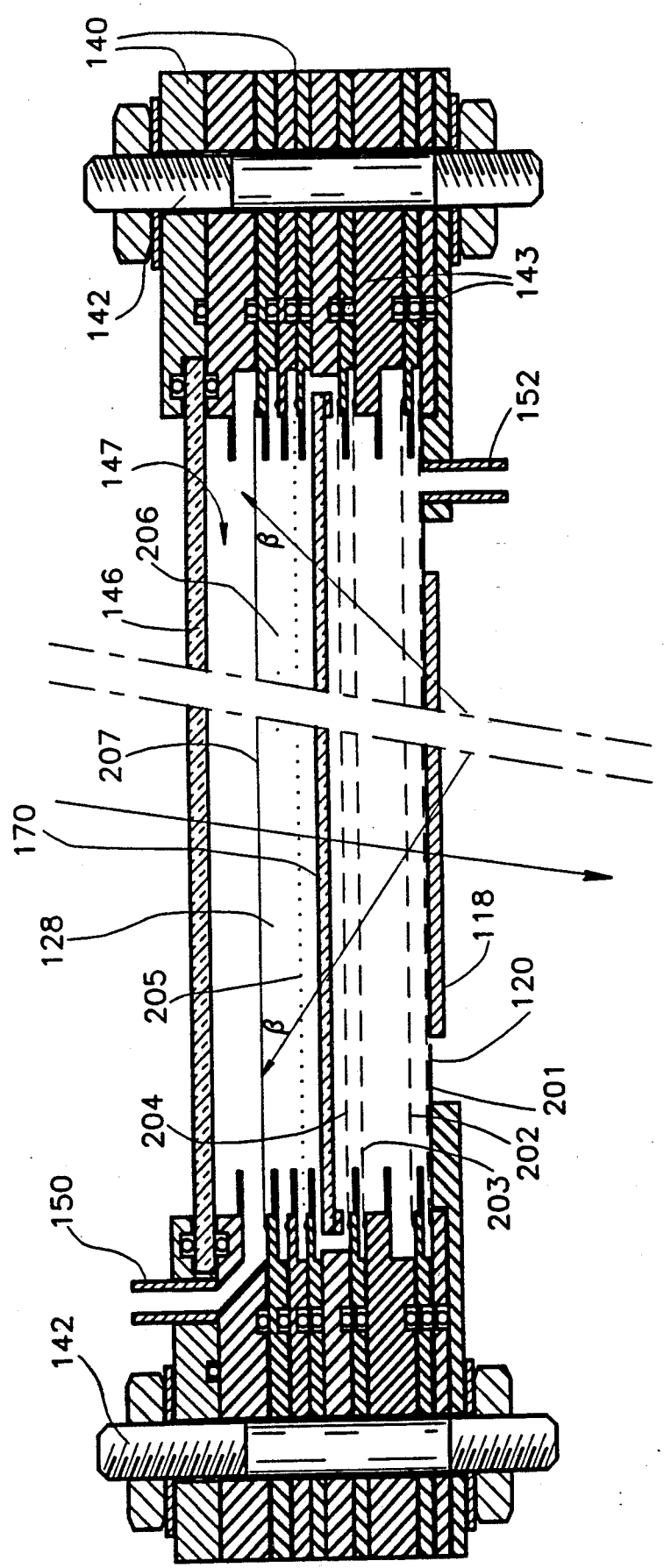
FIG. 11 is a side sectional illustration of an avalanche chamber constructed and operative in accordance with yet another preferred embodiment of the present invention and including a coincidence detector and an optically transparent absorber which is used as a collimator.

Reference is now made to FIG. 11, which illustrates an avalanche chamber similar in structure to that of FIG. 10 and wherein the collimator 119 of FIG. 10 is eliminated and replaced by a collimator 170 located between electrodes 204 and 205. Collimator 170 is preferably an absorption collimator formed of a UV transparent material such as quartz glass of thickness 0.5 mm.

In the embodiment of FIG. 11, coincidence detector 128 is employed to differentiate between those particles which have an angular distribution such that they pass through the collimator 170 and those which do not.

Figure 12:
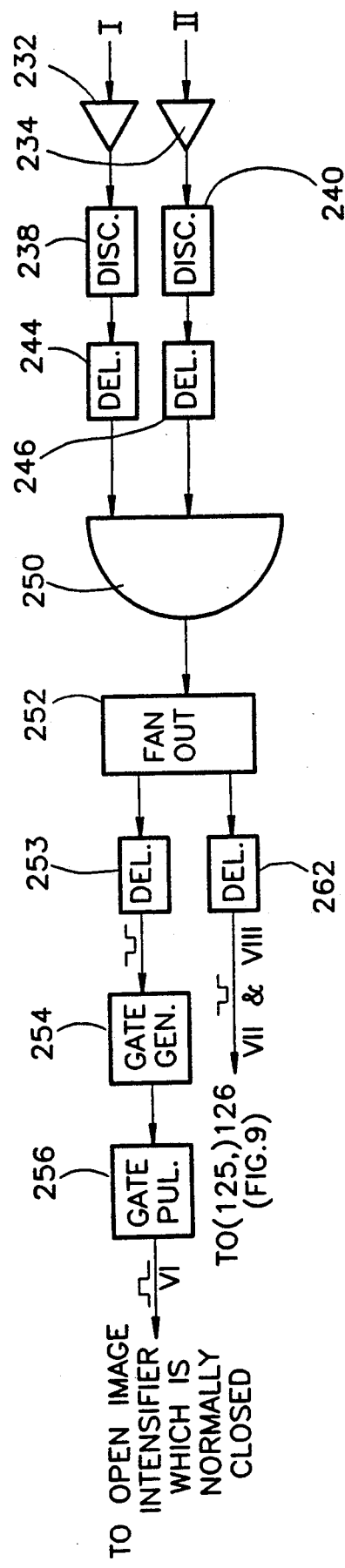
FIG. 12 is a block diagram illustration of an embodiment of gating apparatus useful in the apparatus of FIG. 9.

Reference is now made to FIG. 12, which illustrates an embodiment of logic unit and gate circuit 132. Here, it is seen that the logic unit and gate circuitry 132 comprises two amplifiers 232 and 234, such as LeCroy Model TRA 1000, which output to two respective discriminators 238 and 240, such as LeCroy Model 623B, which in turn output to two respective delay circuits 244 and 246, such as 50 ohm coaxial cables. The outputs of delay circuits 244 and 246 are supplied to AND inputs of a logic unit 250, such as a Lecroy Model 465. The output of logic unit 250 is supplied to a fan out circuit 252, such as a LeCroy Model 430.

One output of fan out circuit 252 is supplied via a delay unit 253 to a gate generator 254, such as a LeCroy Model 222. The output of gate generator 254 activates a gate pulser 256, such as a DEI Model HV 1000, commercially available from DEI of Fort Collins Colo., U.S.A. The output of gate pulser 256 supplies a square wave output VI (FIG. 9) to image intensifier 123, for opening the image intensifier which is normally closed.

A second output of fan out circuit 252 is supplied via a delay circuit 262 as outputs VII and VIII to frame grabber/digitizer 125 and computer 126 (FIG. 9).

It is appreciated that, in accordance with the present invention, amplification of the number of light photons may be provided as set forth in the above-referenced documents by Sauvage et al and by Suzuki et al.

Specifically, Suzuki et al state on page 237, left column, paragraph 2 that "the basic concept behind (a gaseous avalanche chamber followed by an optical readout system) is to recognize ionization tracks through the observation of light emitted from electron avalanches initialized by the charged particles.

Sauvage et al report on the phenomenon of multiplication of light without charge amplification on pages 361-362 as follows: "We transferred the avalanche electrons into a second gap by applying a small drift field . . . Our results show that the emitted light yield is proportional to the transmitted harge, which may be interpreted as a true scintillation process. This is also clearly seen in FIG. 16 where the anode signal of the PM is shown without (a) and with (b) transfer of the charge. The short rise time of the first signal is typical to a charge amplification process while in the second case, the longer rise time reflects a scintillation mechanism during the drift time of electrons along the second gap. This additional light amplification was already used in our application to the optical readout of a UV-detector for RICH . . . "We have demonstrated that, due to a probable direct excitation (scintillation) process, occurring in TMAE mixtures, the light yield increases roughly linearly with the width of the amplification gap. In addition, light amplification can occur, without any further charge amplification, when accelerating initially formed electron swarms across an additional parallel grid gap. We have measured an increase in the light yield of an order of five in such operation condition."

It will be appreciated by persons skilled in the art that the present invention is not limited by what has been particularly shown and described hereinabove. Rather the scope of the present invention is defined only by the claims which follow:

We claim:

1. Apparatus for digital imaging comprising:
   at least one electron multiplier arranged to receive beta radiation from a sample;
   means for collimating the beta radiation without totally blocking all radiation from any location within a given region of interest on the sample and without requiring scanning; and
   readout electrodes operative in response to electrons from the at least one electron multiplier to provide a first output indication of the incidence and location of beta radiation from the sample.

2. Apparatus for digital imaging comprising:
   at least one electron multiplier arranged to receive beta radiation from a sample;
   means for collimating the beta radiation without totally blocking all radiation from any location within a given region of interest on the sample and without requiring scanning;
   a light amplification region providing a multiple photon output indicative of the path of the emitted radiation through the electron multiplier;
   image intensification means for receiving the photon output of the electron multiplier;
   a camera receiving an output from the image intensification means;
   image processing means for receiving the camera output.

3. Apparatus according to claim 1 and wherein said means for collimating comprises a foil located intermediate the sample and at least one of the at least one electron multipliers.

4. Apparatus according to claim 2 and wherein said means for collimating comprises a foil located intermediate the sample and at least one of the at least one electron multipliers.

5. Apparatus according to claim 1 and wherein said means for collimating is arranged downstream of the readout electrodes and there is also provided coincidence sensing means arranged downstream of the collimating means for providing a second output indication of the incidence of electrons thereon corresponding to beta radiation having a predetermined angular distribution and ANDing means for receiving the second output indication from the coincidence sensing means and the first output indication from the readout electrodes for providing a third output indication representative of the location of beta radiation having the predetermined angular distribution.

6. Apparatus according to claim 2 and wherein said means for collimating is arranged downstream of the readout electrodes and there is also provided coincidence sensing means arranged downstream of the collimating means for providing a second output indication of the incidence of electrons thereon corresponding to beta radiation having a predetermined angular distribution and ANDing means for receiving the second output indication from the coincidence sensing means and the first output indication from the readout electrodes for providing a third output indication representative of the location of beta radiation having the predetermined angular distribution.

7. Apparatus according to claim 5 and also comprising electronic readout apparatus for displaying the third output indication.

8. Apparatus according to claim 6 and also comprising electronic readout apparatus for displaying the third output indication.

9. Apparatus according to claim 5 and also comprising means disposed downstream of the coincidence sensing means for providing a fourth output indication of the impingement thereon of cosmic radiation and NAND means responsive to the fourth output indication for generally eliminating indications produced by cosmic radiation in the third output indication.

10. Apparatus according to claim 6 and also comprising means disposed downstream of the coincidence sensing means for providing a fourth output indication of the impingement thereon of cosmic radiation and NAND means responsive to the fourth output indication for generally eliminating indications produced by cosmic radiation in the third output indication.

11. Apparatus according to claim 1 and wherein said collimating means includes a solid plate of predetermined thickness.

12. Apparatus according to claim 2 and wherein said collimating means includes a solid plate of predetermined thickness.

13. Apparatus according to claim 1 and wherein said collimating means includes means for receiving selected collimators having different collimating characteristics.

14. Apparatus according to claim 1 and wherein said at least one electron multiplier comprises a plurality of gas-filled regions separated from each other by wire grids.

15. Apparatus according to claim 2 and wherein said at least one electron multiplier comprises a plurality of gas-filled regions separated from each other by wire grids.

* * * * *